(12) United States Patent
Sandler et al.

(10) Patent No.: US 8,329,861 B2
(45) Date of Patent: Dec. 11, 2012

(54) PROTEIN KTPAF50

(75) Inventors: Tamar Sandler, Ramot Gimmel (IL); Orly Devary, Ramot Gimmel (IL)

(73) Assignee: Two To Biotech Ltd., Jerusalem (IL)

( * ) Notice: Subject to any disclaimer, the term of this patent is extended or adjusted under 35 U.S.C. 154(b) by 30 days.

(21) Appl. No.: 12/810,331

(22) PCT Filed: Dec. 25, 2008

(86) PCT No.: PCT/IL2008/001674
§ 371 (c)(1),
(2), (4) Date: Jun. 24, 2010

(87) PCT Pub. No.: WO2009/083968
PCT Pub. Date: Jul. 9, 2009

(65) Prior Publication Data
US 2010/0286026 A1    Nov. 11, 2010

Related U.S. Application Data

(60) Provisional application No. 61/009,216, filed on Dec. 27, 2007.

(51) Int. Cl.
*C07K 14/47* (2006.01)
*C07K 4/12* (2006.01)
*A61P 35/00* (2006.01)
*A61P 35/02* (2006.01)

(52) U.S. Cl. ....... 530/324; 530/327; 530/830; 514/19.5; 514/19.6

(58) Field of Classification Search .................. None
See application file for complete search history.

(56) References Cited

U.S. PATENT DOCUMENTS
2007/0161031 A1 * 7/2007 Trinklein et al. ............... 435/6

FOREIGN PATENT DOCUMENTS
WO    WO 0056766 A1 *  9/2000
WO    WO 2004093804 A2 * 11/2004

OTHER PUBLICATIONS

Sandler et al (2010. Recent Advances in Clinical Medicine. 168-173).*
Wells (Sep. 18, 1990) "Additivity of Mutational Effects in Proteins." Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) "Powers and Pitfalls in Sequence Analysis: The 70% Hurdle." Genome Research 10:398-400.*
Skolnick et al (2000) "From gene to protein structure and function: novel applications of computational approaches in the genomic era." Trends in Biotech. 18(1): 34-39.*
Doerks et al (1998) "Protein annotation: detective work for function prediction." Trends in Genetics 14(6): 248-250.*
Brenner (1999) "Errors in genome annotation." Trends in Genetics 15(4): 132-133.*

* cited by examiner

*Primary Examiner* — Zachary Howard
(74) *Attorney, Agent, or Firm* — Vorys, Sater, Seymour & Pease LLP; Susanne M. Hopkins; Ari G. Zytcer

(57) ABSTRACT

Provided is a novel, isolated polypeptide including an amino acid sequence of SEQ. ID. NO: 2 or SEQ. ID. NO: 4, and the nucleic acid molecule which encodes it. The polypeptide may be used in a method for treating various diseases including cancer, immune associated, viral and inflammatory diseases.

10 Claims, 4 Drawing Sheets

SEQUENCE LISTING

```
<160> NUMBER OF SEQ ID NOS: 8

<210> SEQ ID NO 1
<211> LENGTH: 222
<212> TYPE: DNA
<213> ORGANISM: Homo sapiens

<400> SEQUENCE: 1
atgccaggcc attctaggct tctgtctatc ctggtttctg gtctgtgcgt tgtgggtagc      60
agcattggcg tattacgccg gagggagcag gctgagcgag gctccagaag gtgcgcaata     120
gccggagagg aaagggcgat gctgtcacct agcccctcc ctgagactcc attcagccca      180
gaaaaaggag ctgctttctc ccccatctac cctaggagaa aa                        222

<210> SEQ ID NO 2
<211> LENGTH: 74
<212> TYPE: PRT
<213> ORGANISM: Homo sapiens

<400> SEQUENCE: 2

Met Pro Gly His Ser Arg Leu Leu Ser Ile Leu Val Ser Gly Leu Cys
1               5                   10                  15

Val Val Gly Ser Ser Ile Gly Val Leu Arg Arg Arg Glu Gln Ala Glu
            20                  25                  30

Arg Gly Ser Arg Arg Cys Ala Ile Ala Gly Glu Glu Arg Ala Met Leu
        35                  40                  45
```

Ser Pro Ser Pro Leu Pro Glu Thr Pro Phe Ser Pro Glu Lys Gly Ala
    50                  55                  60

Ala Phe Ser Pro Ile Tyr Pro Arg Arg Lys
65                  70

<210> SEQ ID NO 3
<211> LENGTH: 150
<212> TYPE: DNA
<213> ORGANISM: Homo sapiens

<400> SEQUENCE: 3
ttacgccgga gggagcaggc tgagcgaggc tccagaaggt gcgcaatagc cggagaggaa      60
agggcgatgc tgtcacctag cccctcccct gagactccat tcagcccaga aaaggagct     120 gctttctccc ccatctaccc taggagaaaa                                     150

<210> SEQ ID NO 4
<211> LENGTH: 50
<212> TYPE: PRT
<213> ORGANISM: Homo sapiens

<400> SEQUENCE: 4

Leu Arg Arg Arg Glu Gln Ala Glu Arg Gly Ser Arg Arg Cys Ala Ile
1               5                   10                  15

Ala Gly Glu Glu Arg Ala Met Leu Ser Pro Ser Pro Leu Pro Glu Thr
            20                  25                  30

Pro Phe Ser Pro Glu Lys Gly Ala Ala Phe Ser Pro Ile Tyr Pro Arg
        35                  40                  45

Arg Lys
    50

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
gcttctgtct atcctggttt ctgg                                            24

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tttctcctag ggtagatggg                                                 20

<210> SEQ ID NO 7
<211> LENGTH: 36
<212> TYPE: PRT
<213> ORGANISM: Artificial Sequence
<220> FEATURE:
<223> OTHER INFORMATION: The N terminal 36 aa of KTPAF50

<400> SEQUENCE: 7

Leu Arg Arg Arg Glu Gln Ala Glu Arg Gly Ser Arg Arg Cys Ala Ile
1               5                   10                  15

Ala Gly Glu Glu Arg Ala Met Leu Ser Pro Ser Pro Leu Pro Glu Thr
            20                  25                  30

```
Pro Phe Ser Pro
        35

<210> SEQ ID NO 8
<211> LENGTH: 14
<212> TYPE: PRT
<213> ORGANISM: Artificial Sequence
<220> FEATURE:
<223> OTHER INFORMATION: The C terminal 14 aa of KTPAF50

<400> SEQUENCE: 8

Glu Lys Gly Ala Ala Phe Ser Pro Ile Tyr Pro Arg Arg Lys
1               5                   10
```

PROTEIN KTPAF50

This is a National Phase Application filed under 35 U.S.C. 371 as a national stage of PCT/IL2008/001674, filed on Dec. 25, 2008, and an application claiming the benefit under 35 USC 119(e) U.S. Provisional Application No. 61/009,216 filed on Dec. 27, 2007, the content of each of which is hereby incorporated by reference in its entirety.

FIELD OF THE INVENTION

This invention relates to a novel protein and therapeutic uses thereof.

The Sequence Listing submitted in text format (.txt) on Jun. 24, 2010, named 1882745_ST25.txt, (created on Monday Mar. 30, 2009, 3.05 KB), is incorporated herein by reference.

BACKGROUND OF THE INVENTION

Diseases which affect human beings may be categorized according to the mechanism of their cause. For example, diseases that have an immunological component or etiology include infectious diseases, acute and chronic inflammatory diseases, cancer, transplantation and autoimmune diseases.

Examples of autoimmune diseases include multiple sclerosis (MS), autoimmune uveitis, autoimmune uveoretinitis, autoimmune thyroiditis, Hashimoto's disease, insulitis, Sjogren's syndrome, spontaneous abortions, experimental autoimmune myocarditis, rheumatoid arthritis (RA), inflammatory bowel disease (IBD), Crohn's disease, lupus (SLE), psoriasis and diabetes, particularly type I.

Additional examples of autoimmune diseases include Acute necrotizing hemorrhagic leukoencephalitis, Addison's disease, Agammaglobulinemia, Allergic asthma, Allergic rhinitis, Alopecia areata, Amyloidosis, Ankylosing spondylitis, Anti-GBM/Anti-TBM nephritis, Antiphospholipid syndrome (APS), Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune thrombocytopenic purpura (ATP), Axonal & neuronal neuropathies, Bal's disease, Behnet's disease, Bullous pemphigoid, Cardiomyopathy, Castleman disease, Celiac sprue (nontropical), Chagas' disease, Chronic fatigue syndrome, Chronic inflammatory demyelinating polyneuropathy (CIDP), Churg-Strauss syndrome, Cicatricial pemphigoid/benign mucosal pemphigoid, Cogan's syndrome, Cold agglutinin disease, Congenital heart block, Coxsackie myocarditis, CREST disease, Essential mixed cryoglobulinemia, Demyelinating neuropathies, Dermatomyositis, Devic disease, Discoid lupus, Dressler's syndrome, Endometriosis, Eosinophilic fasciitis, Erythema nodosum, Experimental allergic encephalomyelitis, Evan's syndrome, Fibromyalgia, Fibrosing alveolitis, Giant cell arteritis (temporal arteritis), Goodpasture's syndrome, Graves' disease, Guillain-Barr syndrome, Hemolytic anemia, Henoch-Schonlein purpura, Herpes gestationis, Hypogammaglobulinemia, Idiopathic thrombocytopenic purpura (ITP), IgA nephropathy, Immunoregulatory lipoproteins, Inclusion body myositis, Insulin-dependent diabetes (type 1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lyme disease, Meniere's disease, Microscopic polyangiitis, Mixed connective tissue disease (MCTD), Mooren's ulcer, Mucha-Habermann disease, Myasthenia gravis, Myositis, Narcolepsy, Neutropenia, Ocular cicatricial pemphigoid, Osteoarthritis, Palindromic rheumatism, Paraneoplastic cerebellar degeneration, Paroxysmal nocturnal hemoglobinuria (PNH), Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Psoriatic arthritis, Idiopathic pulmonary fibrosis, Pyoderma gangrenosum, Pure red cell aplasia, Raynaud's phenomenon, Reflex sympathetic dystrophy, Reiter's syndrome, Relapsing polychondritis, Restless legs syndrome, Rheumatic fever, Sarcoidosis, Schmidt syndrome, Scleritis, Scleroderma, Sperm & testicular autoimmunity, Stiff person syndrome, Subacute bacterial endocarditis (SBE), Sympathetic ophthalmia, Takayasu's arteritis, Temporal arteritis/Giant cell arteritis, Thrombocytopenic purpura (TTP), Autoimmune thyroid disease, Tolosa-Hunt syndrome, Transverse myelitis & necrotizing myelopathy, Ulcerative colitis, Undifferentiated connective tissue disease (UCTD), Vasculitis, Vesiculobullous dermatosis, Vitiligo and Wegener's granulomatosis.

Non-limiting examples of types of cancer include adrenocortical cancer; Malignant melanoma; Non-melanoma skin cancer; Cutaneous T-cell Lymphoma; Kaposi's Sarcoma; Bladder cancer; Colon cancer; Colorectal cancer; Rectal cancer; Neuroectodermal and Pineal cancer; Childhood Brain Stem Glioma; Childhood Cerebellar Astrocytoma; Childhood Cerebral Astrocytoma; Childhood medulloblastoma; Childhood visual pathway Glioma; Meningioma; Mixed Glioma; Oligodendroglioma; Astrocytoma; Ependymoma; Pituitary adenoma; Metastasic Adenocarcinoma; Acoustic neuroma; Paravertebral Malignant teratoma; Breast cancer; Ductal carcinoma; Mammary gland neoplasia; Ovarian cancer; Carcinoid tumour; Cervical cancer; Uterus cancer; Endometrial cancer; Vaginal cancer vulva cancer Gestational Trophoblastic cancer; Fallopain cancer; Uterine sarcoma; Leukemia; Lymphoma (Hodgkin's disease and Non Hodgkin's disease); Neuroblastom; Retinoblastoma; Soft tissue Sarcomas; Wilm's tumour; Fanconi Anaemia; Langerhan's Cells Histiocytosis; Malignant Rhabdoid Tumour of Kidney; Liver cancer; Neuroblastoma; Retinoblastoma; Choriocarcinoma; Endocrine cancers; Endometrial cancer; Esophageal cancer; Ewing's Sarcoma; Eye cancer; Gastric cancer; Gastrointestinal cancers; Genitourinary cancers; Glioma; Gynaecological cancers; Head and neck cancer; Hepatocellular cancer; Hypopharynx cancer; Islet call cancer; Kidney cancer; Laryngeal cancer; Lung cancer; Lymphoma; Male breast cancer; Melanoma; Mesothelioma; Myeloma, multiple; Nasopharyngeal cancer; Non-melanoma Skin cancer; Oesophageal cancer; Osteosarcoma; Ovarian cancer; Pancreas cancer; Pituitary cancer; Prostate cancer; Renal cell carcinoma; Retinoblastoma; Rhabdomyosarcoma; Sarcoma; Skin cancer; Squamous cell carcinoma; Stomach cancer; Testicular cancerthymus cancer; Thyroid cancer; Transitional cells cancer; Trophoblastic cancer; Uterus cancer; Acute Lymphatic leukemia; Acute myeloid leukemia; Adenocystic carcinoma; Anal cancer; Bone cancer; Bowel cancer; Ductal carcinoma; Liposarcoma; Neuroblastoma; Nephroblastoma and Osteosarcoma.

Inflammatory diseases include sepsis, endotoxemia, pancreatitis, uveitis, hepatitis, peritonitis, keratitis, SIRS and injury-induced inflammation.

Diseases linked to fertility include male infertility and female infertility.

Male infertility can be caused by a variety of problems. Some of the more common disorders are listed below.

Deficient Sperm Production: Ninety percent of male infertility is caused by the failure to produce enough sperm. Azzospermia occurs when no sperm is produced while olibospermia is diagnosed when few sperm are produced. Since most sperm are destroyed before ever reaching the egg, the more sperm there are the better the chances that one will successfully fertilize the egg. However, a low sperm count, or a total sperm count of less than 5 million/ml, does not necessarily mean that a man is infertile if the sperm that he does have are healthy, properly formed, and mobile.

Varicocele: A varicose vein around one of the two spermatic cords can cause blood to pool in the testes; this, in turn, causes the temperature to increase in this area. Higher temperatures decrease sperm production and can lead to infertility. Fortunately, this problem can be fixed by surgery.

Other Disorders: Other disorders that can cause male infertility include abnormal development or damage of the testes (caused by endocrine disorders or inflammation), disorders of accessory glands, coital disorders, exposure to diethylstilbestrol (DES) a synthetic estrogen used in the 1950's and 1960's that caused cysts in the male reproductive tract, undescended testicles, and in rare cases genetic disorders such as a chromosomal abnormality.

Female infertility can also be caused by a variety of problems. Some of the more common disorders are listed below.

Polycystic Ovarian Disease: This disease is the most common cause of ovulation disorders in women and is characterized by the presence of many minute cysts in the ovaries, by excess production of androgens, and by infrequent periods (obliomenorrhoea) or absent periods (amenorrhoea). The failure to ovulate is the most common cause of female infertility and can occur for no apparent reason or as the result of stress, hormonal imbalances, and various diseases and disorders of the reproductive system (some of which will be described below).

Pelvic Inflammatory Disease: This infection of the reproductive tract can lead to blocked or damaged fallopian tubes and is usually caused by sexually transmitted disease, miscarriages, abortions, childbirth, or an intrauterine device.

Ovulatory Dysfunction: This disorder occurs when a woman's ovaries are not producing eggs or are producing fewer eggs than usual because of age, hormonal imbalances, or other problems.

Uterine Fibroids: These benign uterine tumors occur in 40% of women and can interfere with embryo implantation or fetal growth.

Endometriosis: This disorder occurs when the tissue which lines the uterus (the endometrium) grows into growths or lesions outside of the uterus (usually on the ovaries, fallopian tubes, and ligaments that support the uterus; the area between the vagina and the rectum; the outer surface of the uterus; the lining of the pelvic cavity; the bladder, bowel, vagina, cervix, vulva, and in abdominal surgical scars). In sync with the menstrual cycle, this tissue builds up, breaks down, and sheds each month; but unfortunately, it has no way of leaving the body. As a result it causes internal bleeding, breakdown of blood and tissue from the lesions, and most often inflammation which can cause pain, infertility, scar tissue formation, adhesions, and bowel problems.

Immunological Infertility: This disorder occurs when the woman's system produces antisperm antibodies which destroy her partner's sperm.

Disorders of carbohydrate metabolism occur in many forms. The most common disorders are acquired. Acquired or secondary derangements in carbohydrate metabolism, such as diabetic ketoacidosis, hyperosmolar coma, and hypoglycemia, all affect the central nervous system. Many forms and variants of peripheral nerve disease also are seen in diabetes. The remaining disorders of carbohydrate metabolism are the rare inborn errors of metabolism (i.e. genetic defects).

The acquired disorders of carbohydrate metabolism are fairly common, both in the United States and internationally. Hypoglycemia is a common cause of neurological disease, especially acute mental deterioration, memory loss, disorientation, obtundation, and coma, among both alcoholics and patients with diabetes who are treated with insulin. Hyperinsulinemia from other causes is rare, but pancreatic tumors could be the cause. Diabetes, with its various neurological complications, is among the most common disorders treated in adult patients. Diabetic ketoacidosis still occurs, though education and close medical follow-up make it less common than it was several decades ago. Hyperosmolar coma is also less a problem than when it was first brought to the attention of internists by Plum and Posner's classic monograph Diagnosis of Stupor and Coma. Hyperosmolar coma still occurs and needs to be kept in mind while evaluating an obtunded patient.

The inherited disorders of carbohydrate metabolism are rare. Severe defects of the pyruvate dehydrogenase (PDH) complex and the benign chemical anomaly called pentosuria have been reported in very few (2-6) patients.

Hypoglycemia, diabetic ketoacidosis, and hyperosmolar coma are all potentially fatal but potentially curable conditions.

SUMMARY OF THE INVENTION

A novel protein, named KTPAF50, has now been discovered, based on a novel cDNA. The peptide encoded by the cDNA is 74 amino acids long and includes a signal peptide of 24 amino acids on its N-terminal end. The cDNA sequence (SEQ. ID. NO: 1) and amino acid sequence (SEQ. ID. NO: 2) of KTPAF50 are as follows:

atgccaggc cattctagg cttctgtct atcctggtt tctggtctg tgcgttgtg ggtagcagc attggcgta ttacgccgg agggagcag gctgagcga ggctccaga aggtgcgca atagccgga gaggaaagg gcgatgctg tcacctagc cccctccct gagactcca ttcagccca gaaaaagga gctgctttc tcccccatc taccctagg agaaaa (SEQ. ID. NO:1)

```
                                        (SEQ. ID. NO: 2)
MPGHSRLLSILVSGLCVVGSSIGVLRRREQAERGSRRCAIAGEERAMLSP
SPLPETPFSPEKGAAFSPIYPRRK
```

Provided by the present invention are thus a nucleic acid molecule of SEQ. ID. NO: 1 and a peptide of SEQ. ID. NO: 2. A polypeptide of SEQ. ID. NO: 2 will be referred to herein as the "full KTPAF50 peptide".

The full KTPAF50 peptide also includes a signal sequence believed to consist of 24 amino acids. Thus, the invention also provides a peptide comprising the sequence of the full KTPAF50 peptide, without the signal peptide, consisting of the following sequence (SEQ ID. NO: 4):

(SEQ ID. NO: 4)
LRRREQAERGSRRCAIAGEERAMLSPSPLPETPFSPEKGAAFSPIYPRRK

The KTPAF50 peptide that is devoid of the signal sequence (SEQ. ID. NO: 4) will be referred to herein as the "KTPAF50 peptide" or "KTPAF50".

Also provided by the invention is a nucleic acid molecule comprising a sequence encoding for the KTPAF50 peptide. This includes the following sequence (SEQ. ID. NO: 3):

ttacgccgg agggagcag gctgagcga ggctccaga aggtgcgca atagccgga gaggaaagg gcgatgctg tcacctagc cccctcct gagactcca ttcagccca gaaaaagga gctgctttc tcccccatc tac-cctagg agaaaa (SEQ. ID. NO:3)

The invention also provides modified nucleic acid molecules of SEQ. ID. NO: 1 or SEQ. ID. NO: 3 and modified peptides of SEQ. ID. NO: 2 or SEQ. ID. NO: 4, in which one or more nucleotides or amino acid residues, respectively, is added, deleted or replaced, without significantly affecting the biological characteristics of the modified molecule as compared to the unmodified molecule.

The term "peptide" is used herein to denote a peptide, polypeptide or protein. The peptide may be obtained synthetically, through genetic engineering methods, expression in a host cell, or through any other suitable means. Unless indicated otherwise, a peptide is generally composed of naturally-occurring L-amino acids.

The term "biological characteristics", with respect to a peptide molecule, refers to the peptide's ability to exert at least one of the in vitro or in vivo effects that may be exerted by the full KTPAF50 peptide or the KTPAF50 peptide, including but not limited to the biological activities described in the specification. For example, biological characteristics include the ability to, treat cancer, immune system associated diseases, viral diseases and inflammatory-based diseases. The term "biological characteristics", with respect to a nucleic acid molecule, refers to the property of encoding a peptide having similar biological characteristics to that of the full KTPAF50 peptide or the KTPAF50 peptide, including, in particular: (i) a nucleic acid molecule that has a different sequence to that of SEQ. ID. NO: 1 or SEQ. ID. NO: 3, but, owing to the redundancy of the genetic code, encodes the full KTPAF50 peptide or the KTPAF50 peptide, respectively; and (ii) a nucleic acid molecule that encodes an amino acid molecule with a different sequence than that of the full KTPAF50 peptide or the KTPAF50 peptide but that has similar biological characteristics to that of the full KTPAF50 peptide or the KTPAF50 peptide, respectively.

The term "without significantly affecting the biological characteristics of the modified molecule as compared to the unmodified molecule" means to denote that the modified molecule retains a biological activity qualitatively similar to that of the unmodified molecule. With respect to a modified peptide, this means that it retains one or more of the biological characteristics of a peptide of SEQ. ID. NO: 2 or SEQ. ID. NO: 4, including, among others, its diagnostic and therapeutic utilities, as specified below, as well as its in vitro and in vivo activities described in the specification. In order to determine whether a peptide retains a biological activity qualitatively similar to that of the unmodified molecule, one or more assays can be carried out, such as for example an in vitro, in vivo or a clinical experiment in which a modified peptide is compared to the corresponding unmodified one (namely that of the full KTPAF50 peptide or the KTPAF50 peptide) that is assayed in parallel; or an experiment in which the modified peptide is assayed to examine whether it has a biological effect similar to that of the unmodified peptide as known from separately conducted experiment. Such an experiment may be carried out, for example, in a manner described in the Examples below. With respect to a modified nucleic acid molecule, the term "without significantly affecting the biological characteristics of the modified molecule as compared to the unmodified molecule" denotes the property of encoding a modified peptide of any of the above characteristics.

A modified peptide may be a peptide that includes a contiguous sequence of at least 8, 12, 15, 20, 25, 30, 35, 40 or at least 45 amino acid residues that has a degree of identity to a corresponding sequence of at least 8, 12, 15, 20, 25, 30, 35, 40 or at least 45 amino acid residues included in the KTPAF50 peptide, the degree of identity being at least 70%, preferably at least 80%, more preferably at least 90% and particularly at least 95%.

The invention further provides a peptide comprising a partial contiguous sequence from the full KTPAF50 peptide including at least 8 amino acid residues, which contiguous sequence is included as a contiguous sequence in said full KTPAF50 peptide. Such a peptide will be referred to herein as a "partial KTPAF50 peptide". Examples of a partial KTPAF50 peptide include, but are not limited to, SEQ. ID. NO:7 and SEQ. ID. NO:8, described in Example VI below.

The invention further provides a protein or polypeptide comprising an amino acid sequence of the full KTPAF50 peptide, KTPAF50 peptide, modified peptide or a partial KTPAF50 peptide (such protein or polypeptide will be referred to herein as "KTPAF50 comprising protein"). The KTPAF50 comprising protein may, for example, be a fusion protein that comprises the full KTPAF50 peptide, the KTPAF50 peptide, a modified peptide or a partial KTPAF50 peptide; it may be a conjugate of a protein or another peptide or polypeptide with the full KTPAF50 peptide, KTPAF50 peptide, modified peptide or partial KTPAF50 peptide; etc.

The invention also provides an oligonucleotide of at least 24 nucleotides that is: (i) an oligonucleotide that encodes a partial contiguous sequence from the KTPAF50 peptide including at least 8 amino acid residues, which may include a contiguous 24 nucleic acid sequence included in SEQ. ID. NO: 1; (ii) a nucleotide sequence that can hybridize to a nucleotide sequence of SEQ. ID. NO: 1 under stringent hybridization conditions; (iii) an oligonucleotide that has a sequence of at least 24 contiguous nucleotides with a degree of identity to a corresponding contiguous sequence of nucleotides included in SEQ. ID. NO: 1 of at least 70%, preferably at least 80%, more preferably at least 90% and particularly at least 95%.

The invention also provides a nucleic acid molecule, e.g. a transfer vector or an expression vector, comprising any of the aforementioned nucleic acid molecules.

Also provided by the invention are modified peptides derived from any of the peptides defined above, e.g., modified peptides in which one or more amino acids are replaced by another amino acid by conservative substitution. As used herein, "conservative substitution" refers to the substitution of an amino acid in one class by an amino acid of the same class, where a class is defined by common physicochemical amino acid side chain properties and high substitution frequencies in homologous proteins found in nature. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu is a conservative substitution.

In one embodiment, only one substitution is made in the amino acid sequence. In another embodiment, two substitutions are made. In a further embodiment, three substitutions are made. The maximum number of substitutions should not exceed that number of amino acids which leaves at least 70%, desirably at least 80%, preferably at least 90%, most preferably at least 95% of the amino acids in the unsubstitued sequence. By one preferred embodiment, the substitutions which include up to 3, at times up to 6 amino acid residues substituted by others, are conservative substitutions.

In a further embodiment, one or more amino acids may be replaced by D-amino acids, preferably the corresponding D-amino acids. In a preferred embodiment, all of the amino acids are D-amino acids.

In a still further embodiment, sequences of the reverse order of the above sequences are also included in the invention.

Thus, also provided by the invention are full KTPAF50 peptides of SEQ ID NO: 2 or preferably KTPAF50 peptides of SEQ ID NO: 4 or partial KTPAF50 sequences thereof, modified by one or more conservative substitutions.

Provided is thus a peptide including at least 10 or 15, or 20, or 25, or 30, or 35, or 40 amino acid residues or the entire sequence of the KTPAF50 peptide.

The invention also includes methods of treatment, methods of diagnosis and pharmaceutical compositions making use of the KTPAF50 peptide, full KTPAF50 peptide, partial KTPAF50 peptide, modified peptide or KTPAF50 comprising protein or of any of the nucleic acid molecules mentioned above. The methods of treatment, methods of diagnosis and pharmaceutical compositions may be used with respect to one or more of the diseases and disorders listed in the background section above.

A pharmaceutical composition according to the invention comprises the KTPAF50 peptide, full KTPAF50 peptide, partial KTPAF50 peptide, modified peptide or KTPAF50 comprising protein or of any of the nucleic acid molecules mentioned above, together with a pharmaceutically acceptable carrier.

By the term "pharmaceutically acceptable carrier" it is meant any one of inert, non-toxic materials, which do not react with the active ingredient. The carrier is selected at times based on the desired form of the formulation. The carrier may also at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. The carriers may be any of those conventionally used and is limited only by chemical-physical considerations, such as solubility and lack of reactivity with the polypeptide, and by the route of administration. The carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way. Typical examples of carriers include (a) liquid solutions, where an effective amount of the active substance is dissolved in diluents, such as water, saline, natural juices, alcohols, syrups, etc.; (b) capsules (e.g. the ordinary hard- or soft-shelled gelatin type containing, for example, surfactants, lubricants, and inert fillers), tablets, lozenges (wherein the active substance is in a flavor, such as sucrose and acacia or tragacanth or the active substance is in an inert base, such as gelatin and glycerin), and troches, each containing a predetermined amount of active agent as solids or granules; (c) powders; (d) suspensions in an appropriate liquid; (e) suitable emulsions; (f) liposome formulation; and others.

Potential diagnostic and therapeutic applications of the KTPAF50 peptide may include one or more of the following:

1. KTPAF50 may serve as a diagnostic tool for lack of immunocompetence after sub-dermal injection of toxins from different organisms.
2. Testing the level of KTPAF50 in the blood may serve as an indicator for the level of immune system activity.
3. The level of KTPAF50 may serve as an indicator of autoimmune diseases.
4. KTPAF50 may serve as a stimulator of the immune system. For example, KTPAF50 may be used to treat a lack of immunocompetence to bacteria, parasites and viral toxins.
5. KTPAF50 may be utilized as a therapeutic tool for decreasing allergic and inflammatory responses. For example, KTPAF50 may be used to decrease the occurrence of asthma or symptoms thereof.
6. KTPAF50 may be used as a therapeutic tool to treat immunodeficiency diseases such as AIDS and combined immunodeficiency.
7. KTPAF50 may be used as a therapeutic tool to treat disorders of glucose metabolism.
9. KTPAF50 may be used to treat several other diseases. For example, KTPAF50 may serve as a suppressor of the immune system to treat autoimmune pathologies such as BDI, myasthenia gravis, multiple sclerosis, diabetes type I, rheumatoid arthritis, systematic lupus, scleroderma, chronic autoimmune hemolytic anemia, colitis and Crohn's disease, etc.
10. KTPAF50 may serve as a stimulator of the immune system to treat cancer diseases such as lung cancer, carcinoma of the larynx, carcinoma of head and neck and breast, Hodgkin's disease, non-Hodgkin's lymphoma, breast cancer, hepato-cellular cancer, melanoma.
11. KTPAF50 may strengthen the immune response of older or younger persons or persons with compromised immune systems.
12. KTPAF50 may be used as a therapeutic tool to treat male or female infertility.
13. KTPAF50 may serve as a general stimulator or inhibitor of different immune reactions and may also affect directly or indirectly other organs like the heart and lung etc.
14. KTPAF50 can serve as a probe to identify specific cells from the immune system and use them for cell therapy.
15. The nucleic acid sequence encoding KTPAF50 or a portion thereof can serve as a probe to identify specific human DNA and cDNA sequences.

For the above diagnostic and therapeutic applications, the full KTPAF50 peptide, a partial KTPAF50 peptide or a KTPAF50 comprising protein, or a modified peptide thereof may also be used.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

EXAMPLE I

Figure 1:
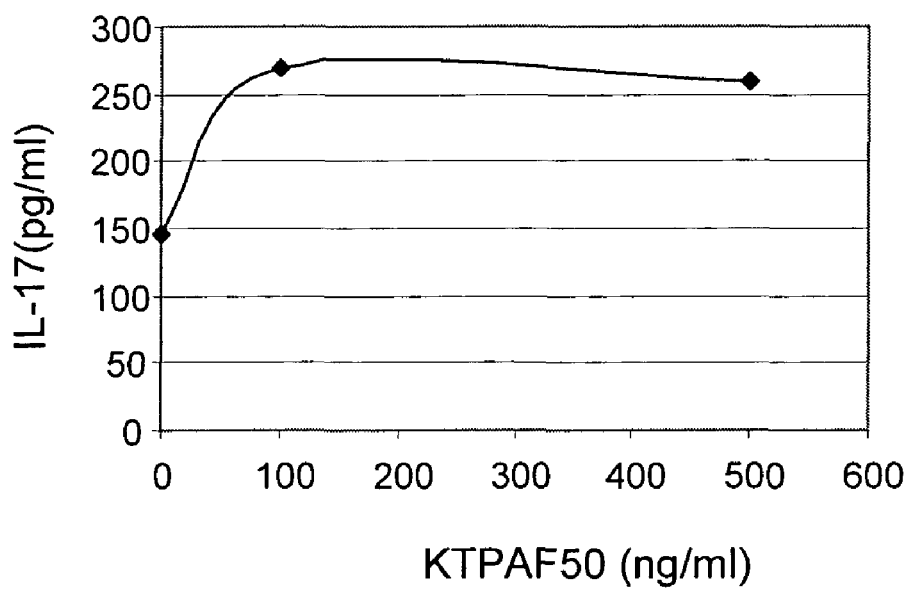
FIG. 1 is a graph showing the secretion of IL-17 (pg/ml) from human peripheral white blood cells treated with the indicated concentrations (ng/ml) of KTPAF50.

A novel cDNA has been isolated from human cDNA libraries.

The following primers were used for RT-PCR analysis:

(SEQ. ID. NO: 5)
5'-GCT TCT GTC TAT CCT GGT TTC TGG-3'

(SEQ. ID. NO: 6)
5'-TTT CTC CTA GGG TAG ATG GG-3'

The following PCR conditions were used:
95° C. for 2 min
40 cycles of:
95° C. for 45 sec
59° C. for 45 sec
72° C. for 5 min
End cycles:
72° C. for 5 min The product of the PCR was sequenced.

Following the PCR analysis on Agarose gels and staining with Cybar Green (Invitrogene), the intensity of the PCR product was evaluated using BioRad ChemiDoc analyzer. The results are as follows:

| cDNA library | Signal | G3PDH | (Signal/G3pdh) | minimal ratio |
|---|---|---|---|---|
| Heart | 3675 | 5434 | 0.676297 | 1.209034 |
| Brain | 3340 | 5971 | 0.55937 | 1.000001 |
| Placenta* | 6029 | 4668 | 1.29156 | 2.308954 |
| Lung | 2929 | 4116 | 0.711613 | 1.272169 |
| Liver | 4809 | 6002 | 0.801233 | 1.432385 |
| Skeletal muscle | 5849 | 6273 | 0.932409 | 1.666891 |
| Kidney* | 8272 | 4069 | 2.032932 | 3.634324 |
| Pancreas* | 8384 | 3898 | 2.150847 | 3.845123 |
| Fetal-Brain | 3721 | 5583 | 0.666488 | 1.522944 |
| Fetal-lung | 4592 | 5554 | 0.826792 | 1.889243 |
| Fetal-liver | 4424 | 5525 | 0.800724 | 1.829678 |
| Fetal-kidney* | 4635 | 3729 | 1.242961 | 2.840202 |
| Fetal-Heart | 2291 | 5235 | 0.437631 | 1.000001 |
| Fetal-Spleen | 3845 | 6827 | 0.563205 | 1.28694 |
| Fetal-Thymus | 3013 | 5133 | 0.586986 | 1.341281 |
| Fetal-skeletal-muscle | 2821 | 4754 | 0.593395 | 1.355926 |
| Spleen | 5476 | 22116 | 0.247604 | 1.179064 |
| Thymus | 4678 | 20038 | 0.233456 | 1.111697 |
| Prostate | 4685 | 19662 | 0.238277 | 1.134652 |
| Testis* | 5710 | 19003 | 0.300479 | 1.430852 |
| Ovary | 4435 | 18072 | 0.245407 | 1.168606 |
| S. intestine | 3247 | 15424 | 0.210516 | 1.002458 |
| colon | 2779 | 11847 | 0.234574 | 1.11702 |
| resting CD14 | 1185 | 11165 | 0.106135 | 1.061352 |
| resting CD8* | 1132 | 10042 | 0.112727 | 1.127265 |
| resting CD4 | 1946 | 8932 | 0.217868 | 2.178683 |
| Mononuclear* | 869 | 8204 | 0.105924 | 1.059239 |
| activated CD8* | 2406 | 8535 | 0.281898 | 2.818981 |
| activated CD4 | 1979 | 9065 | 0.218312 | 2.183122 |
| activated mononuclear* | 1695 | 7082 | 0.239339 | 2.393392 |
| resting CD19* | 2668 | 6365 | 0.419167 | 4.191673 |
| activated CD19* | 1635 | 7140 | 0.228992 | 2.289916 |

*significant results

It may be seen that the main tissues where the cDNA is expressed are: kidney, pancreas, testis and placenta. Interestingly, the product was also expressed in leukocytes and its expression varied with relation to the cells' activation.

EXAMPLE II

In order to determine the potential effect of KTPAF50 on various diseases, KTPAF50 was incubated with human peripheral white blood cells (pWBC), and the amounts of a panel of cytokines were measured.

KTPAF50 was chemically synthesized by Anaspec Inc.

Total human white blood cells were cultured in PHA containing medium (Biological Industries INC—catalogue number—01-201-1) (2 million cells/well in 2 ml medium). The cells were treated for 3 days with KTPAF50 at the concentrations indicated in the figures. The control cells were not treated.

Figure 2:
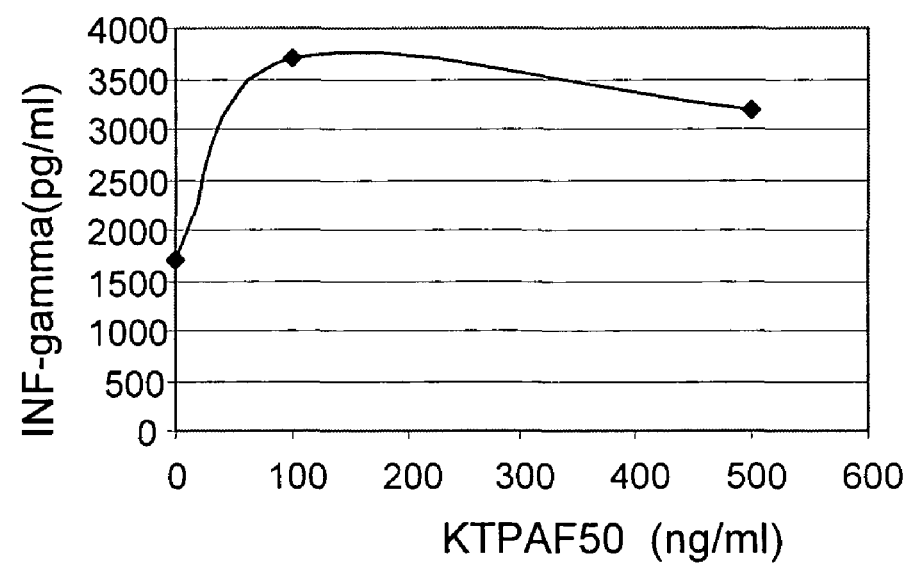
FIG. 2 is a graph showing the secretion of INF-γ (pg/ml) from human peripheral white blood cells treated with the indicated concentrations (ng/ml) of KTPAF50.
Figure 3:
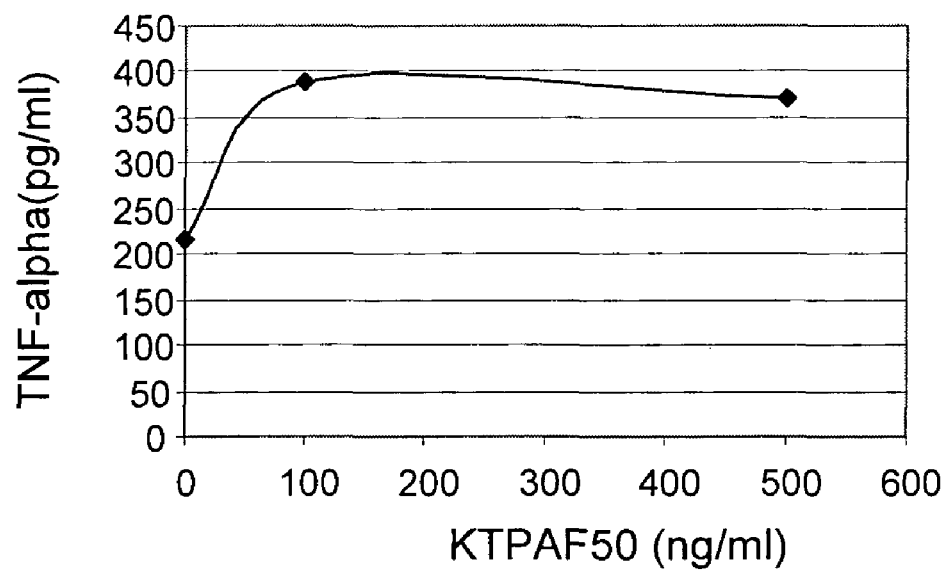
FIG. 3 is a graph showing the secretion of TNF-α (pg/ml) from human peripheral white blood cells treated with the indicated concentrations (ng/ml) of KTPAF50.

At day 3 medium was harvested and subjected to ELISA analysis, using e-Bioscience kits for human IL-17 (catalogue number: 88-7176), human INF-γ (catalogue number: 88-7316) and human TNF-α (catalogue number: 88-7346. The results are summarized in FIGS. 1, 2 and 3.

It may be seen that KTPAF50 stimulated the pWBC to secrete all three cytokines measured. The secretion of IL-17 indicates that KTPAF50 can have a pro-inflammatory role. The secretion of INF-γ indicates that KTPAF50 can have an anti-viral, an anti-cancer and a pro-inflammatory role. The secretion of TNF-α indicates that KTPAF50 can have a role in stimulating the immune system.

EXAMPLE III

In order to further determine the effect of KTPAF50 on cancer, KTPAF50 was incubated with cancer cell lines.

U937 acute myeloid leukemia cells and PC3 prostate cancer cells were each grown in 10% FCS+RPMI medium and quadruplicates were inoculated into a 96 well plate, 20,000 cells/well.

Figure 4:
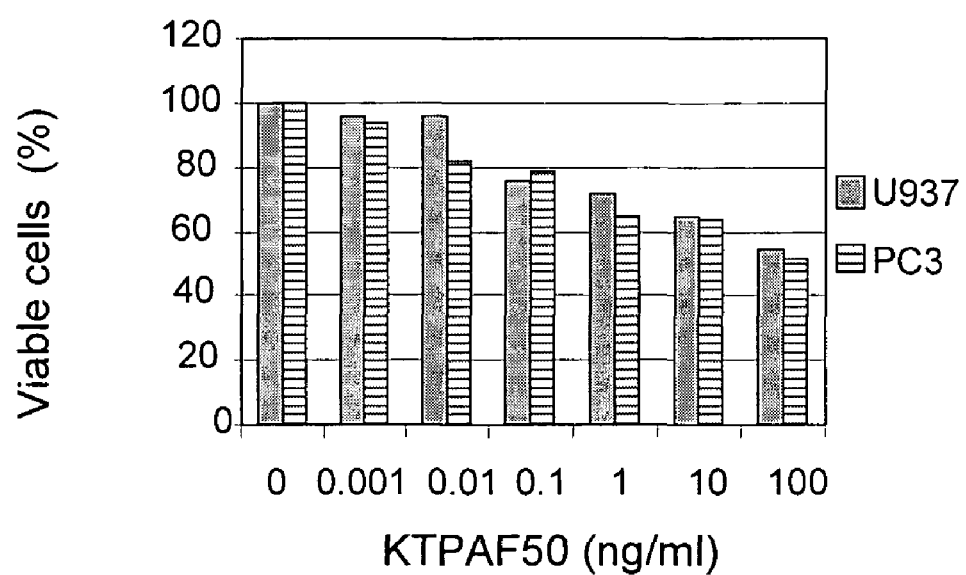
FIG. 4 is a bar graph showing the % of viable cells (normalized to the control amount) as a function of KTPAF50 concentration (ng/ml)

KTPAF50 was incubated with the cells for one day, and viable cells were detected using Resazurin (R&D System) and a spectrophotometer. The results are presented in FIG. 4.

It may be seen that KTPAF50 causes a significant decrease in viable cells from two types of cancer.

EXAMPLE IV

To further investigate the role of KTPAF50 in the immune response, the presence of KTPAF50 in various immune cytotoxic cells was determined.

Figure 5:
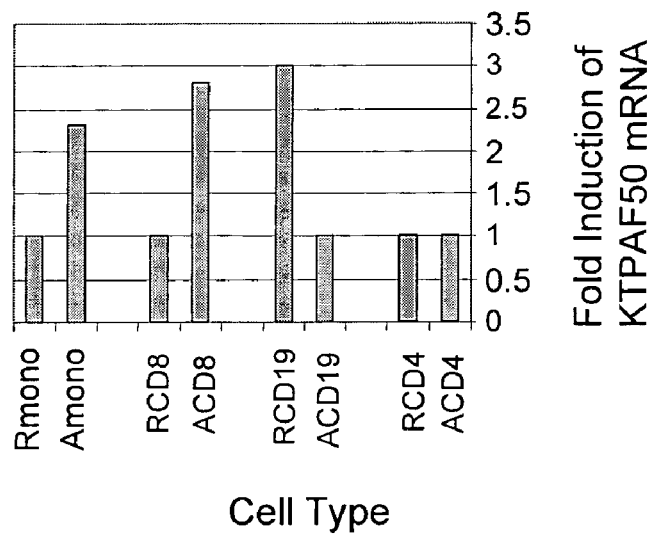
FIG. 5 is a bar graph showing the degree of induction of KTPAF50 mRNA in various types of cells involved in the immune cytotoxic response.

Human cDNA libraries of the following cells were purchased from Clontech Ltd:
1. mono—resting (R) and activated (A) monocytes (the cells were activated using LPS or PHA)
2. CD8 —R and A cytotoxic CD8 T cells
3. CD19 —R and A CD19 B cells
4. CD4 —R and A CD4 T helper cells Quantitative analysis of KTPAF50 mRNA in these cells was carried out by RT-PCR methods using specific primers of KTPAF50. The results are summarized in FIG. 5.

It may be seen that activation of monocytes and cytotoxic T cells results in a significant increase in the expression of KTPAF50, while activation of B cells brings about a decrease in KTPAF50 expression. Activation or deactivation of T helper cells had no effect on KTPAF50 expression. Thus, KTPAF50 may be used as a marker for activation of cellular immune response, and for identifying TH1 vs. Th2 pathways.

EXAMPLE V

The effect of KTPAF50 on cancer cells was also tested in vivo.

14 athymic nude female 8-9 week-old mice were purchased from Harlan Biotech, Israel. The mice were inoculated s.c. with $15 \times 10^6$ U937 cells. Tumors began to grow, and at day 9 the mice were divided into 2 groups:
- A control group which was injected with saline.
- A treated group which was injected with KTPAF50 (25 ug/mouse)

Figure 6:
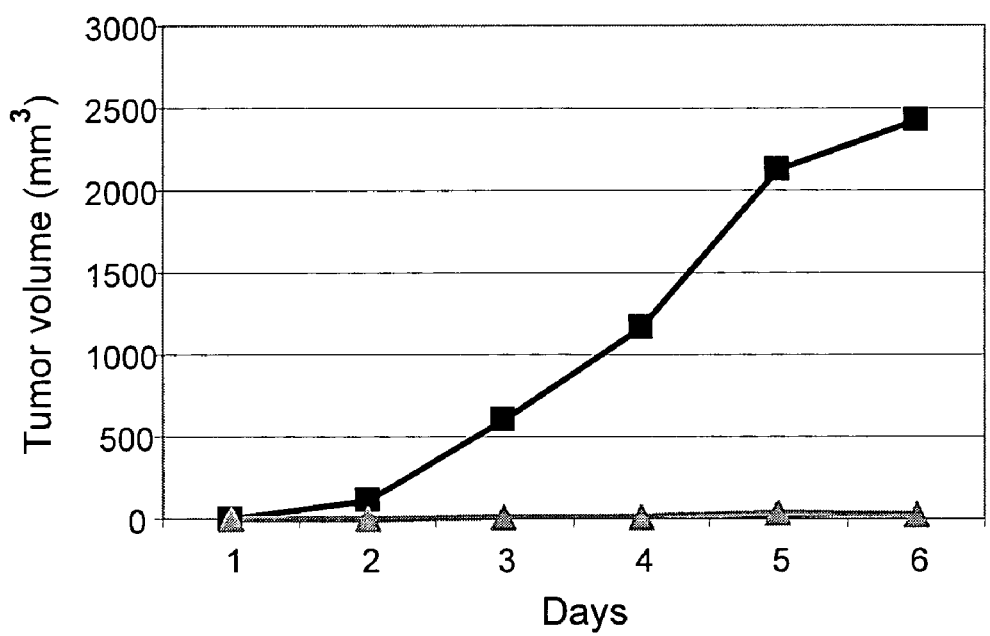
FIG. 6 is a graph showing U937 tumor volume ($mm^3$) in treated (▲) and untreated (■) (control) nude mice as a function of time.

At day 20, 4 mice from the control group were sacrificed due to ethical reasons because they had huge tumors. The results are presented in FIG. 6.

The striking results show that KTPAF50 totally prevented tumor growth.

EXAMPLE VI

In order to determine whether the entire KTPAF50 peptide is required for activity, the experiment described in Example III above, using U937 cells, was repeated with the complete KTPAF50 peptide and fragments thereof.

The following KTPAF50 peptides were used:
A—the KTPAF50 peptide (50 amino acids)
B—the N terminal 36 aa of KTPAF50

```
                                            (SEQ. ID. NO: 7)
(LRRREQAERGSRRCAIAGEERAMLSPSPLPETPFSP)
                                            (SEQ. ID. NO: 8)
C - the C terminal 14 aa of KTPAF50 (EKGAAFSPIYPRR
K)
```

Figure 7:
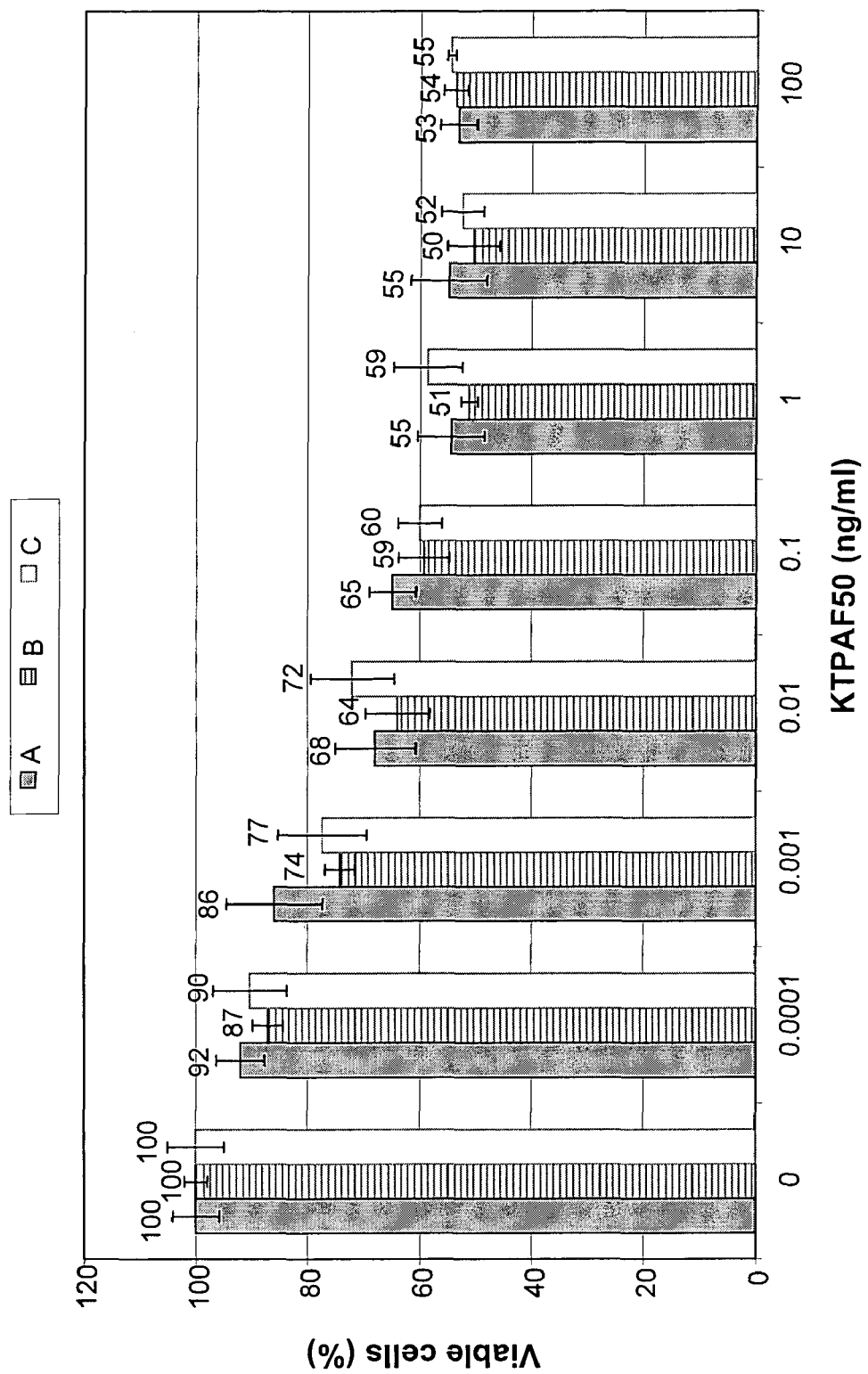
FIG. 7 is a bar graph showing the % of viable cells (normalized to the control amount) as a function of concentration (ng/ml) of KTPAF50 peptide and fractions thereof. A: the KTPAF50 peptide; B: the N terminal 36 aa of KTPAF50; C: the C terminal 14 aa of KTPAF50.

The results are summarized in FIG. 7.

It may be seen that the KTPAF50 fractions have anti-cancer activity similar to the KTPAF50 peptide.

---

The invention claimed is:

1. An isolated polypeptide comprising the amino acid sequence of SEQ. ID. NO: 2 or SEQ. ID. NO: 4.

2. An isolated polypeptide comprising the amino acid sequence of SEQ. ID. NO: 2 or SEQ. ID. NO: 4, in which one or more amino acid residues is added, deleted or substituted, wherein the isolated polypeptide, as modified, retains a biological activity qualitatively similar to that of the polypeptide when unmodified, the biological activity being selected from the group consisting of stimulating peripheral white blood cells to secrete IL-17, INF-γ, and TNF-α, causing a decrease in viable U937 acute myeloid leukemia cells, causing a decrease in viable PC3 prostate cancer cells and preventing growth of tumors originating in U937 cells, and further wherein said isolated polypeptide comprises the sequence of SEQ. ID. NO: 7 or SEQ. ID. NO: 8.

3. An isolated polypeptide comprising a partial contiguous sequence from SEQ. ID. NO: 4 that includes at least 20 amino acid residues, which contiguous sequence is included as a contiguous sequence in the amino acid sequence of SEQ. ID. NO: 4, wherein the isolated polypeptide, as modified, retains a biological activity qualitatively similar to that of SEQ. ID. NO: 4, and
wherein the biological activity is selected from the group consisting of stimulating peripheral white blood cells to secrete IL-17, INF-γ, and TNF-α, causing a decrease in viable U937 acute myeloid leukemia cells, causing a decrease in viable PC3 prostate cancer cells and preventing growth of tumors originating in U937 cells, and further wherein said isolated polypeptide comprises the sequence of SEQ. ID. NO: 7 or SEQ. ID. NO: 8.

4. An isolated polypeptide comprising the amino acid sequence of SEQ. ID. NO: 7 or SEQ. ID. NO:8.

5. The isolated polypeptide according to claim 1, comprising a modified sequence of SEQ. ID. NO: 4, in which up to three residues are each independently substituted by another amino acid residue by conservative substitution,
wherein the isolated polypeptide, as modified, retains a biological activity qualitatively similar to that of SEQ. ID. NO: 4, and
wherein the biological activity is selected from the group consisting of stimulating peripheral white blood cells to secrete IL-17, INF-γ, and TNF-α, causing a decrease in viable U937 acute myeloid leukemia cells, causing a decrease in viable PC3 prostate cancer cells and preventing growth of tumors originating in U937 cells.

6. A pharmaceutical composition comprising the isolated polypeptide of claim 1.

7. A pharmaceutical composition comprising the isolated polypeptide of claim 2.

8. A pharmaceutical composition comprising the isolated polypeptide of claim 3.

9. A pharmaceutical composition comprising the isolated polypeptide of claim 4.

10. A pharmaceutical composition comprising the isolated polypeptide of claim 5.

* * * * *